United States Patent
Wu et al.

(10) Patent No.: US 10,118,911 B2
(45) Date of Patent: Nov. 6, 2018

(54) P-TOLUENESULFONATE FOR MEK KINASE INHIBITOR, AND CRYSTAL FORM THEREOF AND PREPARATION METHOD THEREFOR

(71) Applicant: Jiangsu Hengrui Medicine Co., Ltd., Lianyungang, Jiangsu (CN)

(72) Inventors: Guaili Wu, Jiangsu (CN); Xiaohui Gao, Jiangsu (CN); Lin Bian, Jiangsu (CN); Junlei Jia, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/559,516

(22) PCT Filed: Mar. 8, 2016

(86) PCT No.: PCT/CN2016/075853
§ 371 (c)(1),
(2) Date: Sep. 19, 2017

(87) PCT Pub. No.: WO2016/155473
PCT Pub. Date: Oct. 6, 2016

(65) Prior Publication Data
US 2018/0118715 A1    May 3, 2018

(30) Foreign Application Priority Data

Mar. 27, 2015 (CN) .......................... 2015 1 0141303

(51) Int. Cl.
C07D 401/12    (2006.01)
A61K 31/4412    (2006.01)
C07D 213/82    (2006.01)
C07D 405/12    (2006.01)
A61P 35/00    (2006.01)

(52) U.S. Cl.
CPC ........ C07D 401/12 (2013.01); A61K 31/4412 (2013.01); A61P 35/00 (2018.01); C07D 213/82 (2013.01); C07D 405/12 (2013.01); C07B 2200/13 (2013.01)

(58) Field of Classification Search
CPC . A61K 31/4412; A61P 35/00; C07B 2200/13; C07D 213/82; C07D 401/12; C07D 405/12
See application file for complete search history.

(56) References Cited

U.S. PATENT DOCUMENTS

2010/0063053 A1    3/2010    Marlow et al.
2012/0238599 A1    9/2012    Lee et al.
2016/0244410 A1*    8/2016    Tu ........................ C07D 213/82

FOREIGN PATENT DOCUMENTS

CN    102459188 A    5/2012
WO    2009129938 A1    10/2009
WO    2015058589 A1    4/2015

OTHER PUBLICATIONS

Int'l Search Report dated Jun. 3, 2016 in Int'l Application No. PCT/CN2016/075853.

* cited by examiner

*Primary Examiner* — Valerie Rodriguez-Garcia
(74) *Attorney, Agent, or Firm* — Panitch Schwarze Belisario & Nadel LLP (57) ABSTRACT

Disclosed are a p-toluenesulfonate of a MEK kinase inhibitor, and a crystal form thereof and a preparation method thereof. Specifically disclosed are a 2-((2-fluorine-4-iodophenyl)amino)-1-methyl-4-((6-methylpyridine-3-group)oxygroup)-6-carbonyl-1,6-dihydropyridine-3-formamide p-toluenesulfonate (a compound represented by formula (I)), a crystal form I, and a preparation method thereof. The obtained crystal form I of the compound of formula (I) has good crystal form stability and chemical stability, and the crystallization solvent used has low toxicity and low residue, and is more suitable for use in clinical treatment.

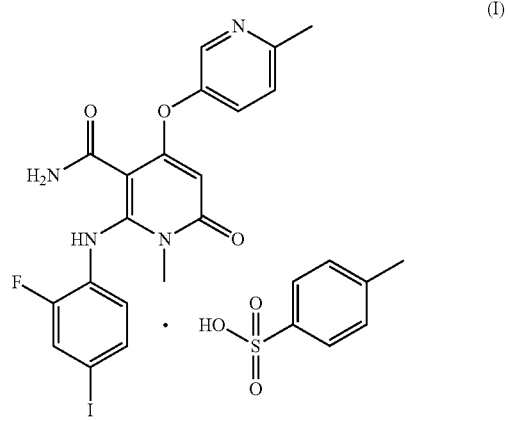

18 Claims, 2 Drawing Sheets

P-TOLUENESULFONATE FOR MEK KINASE INHIBITOR, AND CRYSTAL FORM THEREOF AND PREPARATION METHOD THEREFOR

CROSS-REFERENCE TO RELATED APPLICATION

This application is a Section 371 of International Application No. PCT/CN2016/075853, filed Mar. 8, 2016, which was published in the Chinese language on Oct. 6, 2016, under International Publication No. WO 2016/155473 A1, and the disclosure of which is incorporated herein by reference.

FIELD OF THE INVENTION

The present invention relates to a p-toluenesulfonate of a MEK kinase inhibitor and crystal form I thereof, particularly a 2-((2-fluoro-4-iodophenyl)amino)-1-methyl-4-((6-methylpyridin-3-yl)oxy)-6-oxo-1,6-di hydropyridine-3-carboxamide p-toluenesulfonate and crystal form I thereof.

BACKGROUND OF THE INVENTION

Melanoma is one of the more common malignant tumors in clinical practice, and it is also one of the fastest growing malignant tumors with an annual growth rate of 3-5%. The annual number of new cases of melanoma around the world is 199,627, and the number of deaths is 46,327. Although the incidence of melanoma is low in China, it has multiplied in recent years. In China, the incidence in 2000 was merely 0.2/100,000, but the incidence in 2005-2007 was 1/100,000, and the annual number of new cases is about 20,000. Therefore, melanoma has become one of the diseases that seriously threatens the health of Chinese people.

Presently in China, the study of drugs for the treatment of this disease is still in the initial stages. The drugs Vemurafenib tablet and Ipilimumab (a monoclonal antibody) are useful for the treatment of melanoma, but these two drugs may cause other skin diseases, such as squamous cell carcinoma and the like, while exerting their activity. Therefore, it is of great importance to find effective drugs for the treatment of melanoma.

According to feedbacks from clinical studies, MEK kinase inhibitors have excellent efficacy against the "king of cancers", i.e. advanced melanoma. Therefore, MEK kinase inhibitors have become a hot anti-cancer target, for which many major companies compete to develop.

The international patent application PCT/CN2014/085976 from the present applicant provides a MEK kinase inhibitor of the following formula, the chemical name of which is 2-((2-fluoro-4-iodophenyl)amino)-1-methyl-4-((6-methylpyridin-3-yl)oxy)-6-oxo-1,6-di hydropyridine-3-carboxamide. It was found that this compound has strong inhibitory activity against MEK kinase. It has the potential to be developed as a new drug for the treatment of melanoma, and provides a new therapeutic option for melanoma patients.

It is known by those skilled in the art that a compound in the form of a free base is usually pharmaceutically unacceptable due to defects in its properties. For most drugs, it is necessary to provide active compounds in other forms in order to improve these defects, and a common solution is to transform compounds in the free base form into pharmaceutically acceptable salts thereof. In addition, the crystal structure of the pharmaceutically active ingredient often affects the chemical stability of the drug. Different crystallization conditions and storage conditions can lead to changes in the crystal structure of the compound, and sometimes the accompanying production of other forms of crystal form. In general, an amorphous drug product does not have a regular crystal structure, and often has other defects, such as poor product stability, smaller particle size, difficult filtration, easy agglomeration, and poor liquidity. Therefore, it is necessary to improve the various properties of the above product. There is a need to find a new crystal form with high purity and good chemical stability.

SUMMARY OF THE INVENTION

The present invention provides a 2-((2-fluoro-4-iodophenyl)amino)-1-methyl-4-((6-methylpyridin-3-yl)oxy)-6-oxo-1,6-di hydropyridine-3-carboxamide p-toluenesulfonate (as shown in formula (I)).

The compound of formula (I) can be obtained by reacting p-toluenesulfonic acid with 2-((2-fluoro-4-iodophenyl)amino)-1-methyl-4-((6-methylpyridin-3-yl)oxy)-6-oxo-1,6-di hydropyridine-3-carboxamide.

Compared to 2-((2-fluoro-4-iodophenyl)amino)-1-methyl-4-((6-methylpyridin-3-yl)oxy)-6-oxo-1,6-di hydropyridine-3-carboxamide, the solubility and bioavailability of the compound of formula (I) has been greatly improved, and the compound of formula (I) is more pharmaceutically acceptable.

Figure 1:
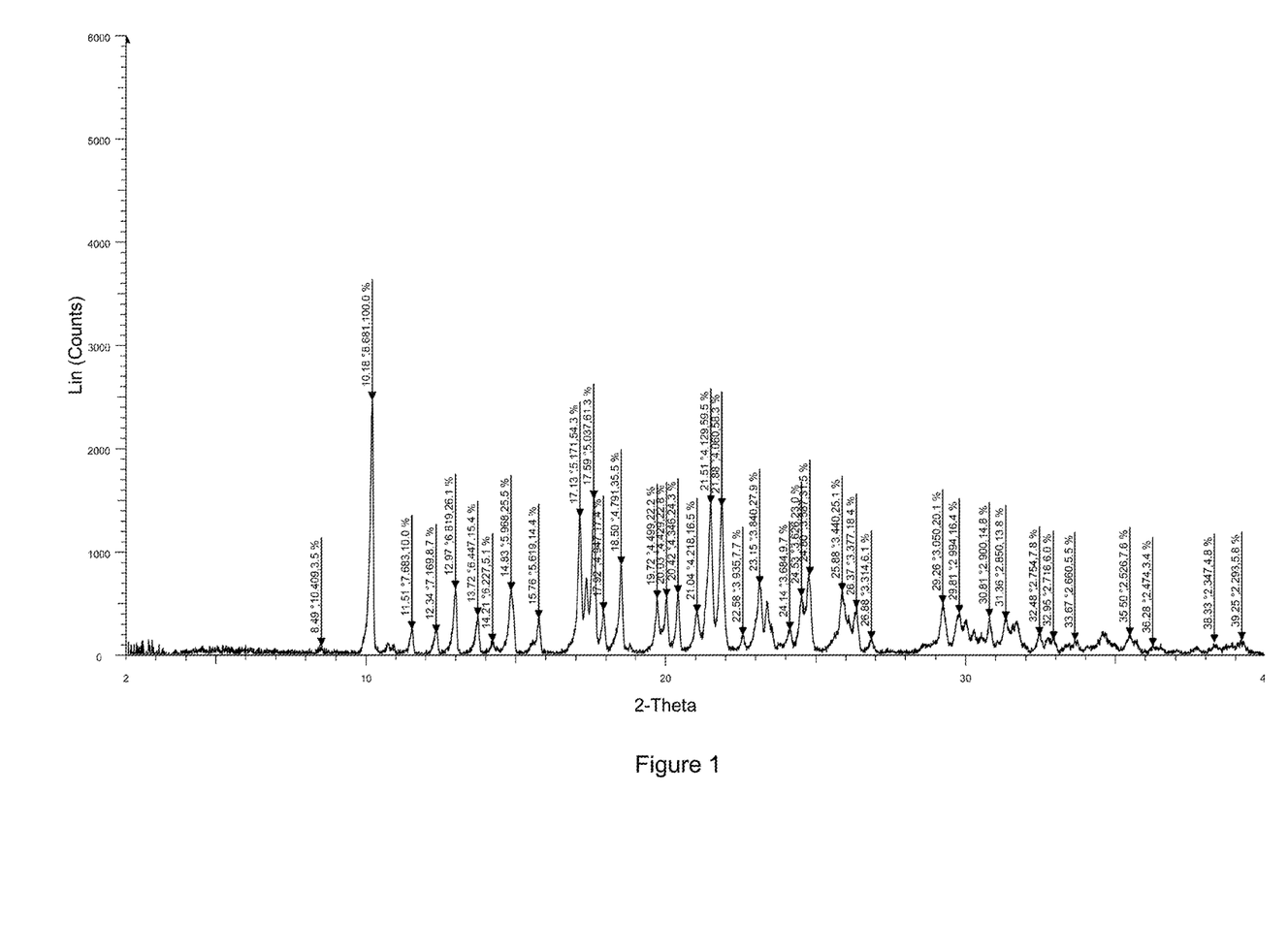
FIG. 1 shows the X-ray powder diffraction spectrum of crystal form I of the compound of formula (I).

A series of crystal products of the compound of formula (I) have been obtained under various crystallization conditions, and X-ray diffraction and differential scanning calorimetry (DSC) measurements have been conducted on the obtained crystal products. It was found that a stable crystal form of the compound of formula (I), which is referred to as crystal form I, can be obtained under specific crystallization conditions of the present invention. The DSC spectrum of crystal form I of the present application shows a melting endothermic peak at about 237° C. The X-ray powder diffraction spectrum, which is obtained by using Cu-Ka radiation and represented by 2θ angle and interplanar distance (d value), is shown in FIG. 1, in which there are characteristic peaks at about 10.18 (8.68), 11.51 (7.68), 12.34 (7.17), 12.97 (6.82), 13.72 (6.45), 14.83 (5.97), 15.76 (5.62), 17.13 (5.17), 17.59 (5.04), 17.92 (4.95), 18.50 (4.79), 19.72 (4.50), 20.03 (4.43), 20.42 (4.35), 21.04 (4.22), 21.51 (4.13), 21.88 (4.06), 23.15 (3.84), 24.14 (3.68), 24.53 (3.63), 24.77 (3.59), 25.88 (3.44) and 26.37 (3.38).

The present invention also provides a method of preparing crystal form I of 2-((2-fluoro-4-iodophenyl)amino)-1-methyl-4-((6-methylpyridin-3-yl)oxy)-6-oxo-1,6-di hydropyridine-3-carboxamide p-toluenesulfonate. The method comprises the following steps of:

(1) dissolving p-toluenesulfonic acid and 2-((2-fluoro-4-iodophenyl)amino)-1-methyl-4-((6-methylpyridin-3-yl)oxy)-6-oxo-1,6-di hydropyridine-3-carboxamide, or any crystal form or amorphous form of the compound of formula (I) into an organic solvent or a mixed solvent of an organic solvent and water to precipitate a crystal, wherein the organic solvent is selected from one or more of alcohols, ketones, nitriles and ethers having 3 or less carbon atoms; and (2) filtering the crystal, then washing and drying it.

In a preferred embodiment of the present invention, in step (1), the organic solvent is preferably methanol, ethanol or isopropanol; the mixed solvent of organic solvent and water is preferably methanol/water, ethanol/water, isopropanol/water, acetonitrile/water, acetone/water or tetrahydrofuran/water.

Further, the most preferred single solvent is isopropanol.

In an embodiment of the present invention, the preferred mixed solvent is acetone/water, and the ratio of the two is not particularly limited. In a preferred embodiment of the present invention, the volume ratio of the two is 9:1.

The recrystallization method is not particularly limited, and can be carried out by a conventional recrystallization process. For example, the material, i.e., the compound of formula (I), can be dissolved in a solvent under heating, and then the solution is cooled slowly to precipitate a crystal. After the completion of crystallization, the desired crystal can be obtained via filtering and drying. In particular, the crystal obtained by filtration is usually dried in a vacuum under reduced pressure at a heating temperature of about 30 to 100° C., preferably 40 to 60° C., to remove the recrystallization solvent.

The resulting crystal form of the compound of formula (I) is determined by DSC and X-ray diffraction spectra. Meanwhile, the residual solvent in the obtained crystal is also determined.

Crystal form I of the compound of formula (I) prepared according to the method of the present invention does not contain or contains only a relatively low content of residual solvent, which meets the requirement of the National Pharmacopoeia concerning the limitation of residual solvent of drug products. Therefore, the crystal of the present invention is suitable for use as a pharmaceutical active ingredient.

The research results show that crystal form I of the compound of formula (I) prepared according to present invention is stable under conditions of high temperature and high humidity, and that crystal form I is also stable under conditions of grinding, pressure and heating, which meets the production, transportation and storage requirements of drug products. The preparation process thereof is stable, reproducible and controllable, which is suitable for industrial production.

DETAILED DESCRIPTION OF THE INVENTION

The present invention is illustrated by the following examples in detail. The examples of the present invention are merely intended to describe the technical solution of the present invention, and should not be considered as limiting the scope of the present invention.

Test Instruments Used in the Experiments

1. DSC spectrum

Instrument type: Mettler Toledo DSC 1 Stare$^e$ System
Purging gas: Nitrogen
Heating rate: 10.0° C./min
Temperature range: 40-300° C.

2. X-ray diffraction spectrum

Instrument type: Bruker D8 Focus X-ray powder diffractometer
Ray: monochromatic Cu-Kα ray (λ=1.5406)
Scanning mode: θ/2θ, Scanning range: 2-40°
Voltage: 40 KV, Electric current: 40 mA Example 1: Preparation of 2-((2-fluoro-4-iodophenyl)amino)-1-methyl-4-((6-methylpyridin-3-yl)oxy)-6-oxo-1,6-dihydropyridine-3-carboxamide -continued

Step 1

1-(2-fluoro-4-iodophenyl)urea 2-fluoro-4-iodoaniline 1a (50.80 g, 214 mmol) was dissolved in 254 mL of trichloromethane, followed by addition of triethylamine (60 mL, 429 mmol). The reaction solution was cooled down to 0° C., and added with N,N-carbonyldiimidazole (69.50 g, 429 mmol). After stirring for 15 minutes, the reaction solution was warmed up to room temperature and stirred for 4 hours. The reaction solution was cooled down to 0° C., then added with 254 mL of ammonia water and filtered. The filter cake was washed with water (50 mL×2), trichloromethane (20 mL×2) and ethyl acetate (50 mL×2) successively, and dried to obtain the crude title compound 1-(2-fluoro-4-iodophenyl)urea 1b (53 g, white solid), which was used directly in the next step without further purification.

MS m/z (ESI): 281.0 [M+1]

Step 2

2-cyano-N-((2-fluoro-4-iodophenyl)carbamoyl)acetamide

The crude 1-(2-fluoro-4-iodophenyl)urea 1b (113 g, 404 mmol) was dissolved in 450 mL of N,N-dimethylformamide, followed by addition of 2-cyanoacetic acid (41 g, 488 mmol). After cooling down to 0° C., the reaction solution was added with methanesulfonyl chloride (55.44 g, 484 mmol), then warmed up to room temperature and stirred for 2 hours. The reaction solution was added with 780 mL of a mixed solution of water and isopropanol (V:V=1:2), stirred for 1 hour, and filtered. The filter cake was washed with water (200 mL×2) and ethyl acetate (50 mL) successively, and dried to obtain the crude title compound 2-cyano-N-((2-fluoro-4-iodophenyl)carbamoyl)acetamide 1c (143 g, white solid), which was used directly in the next step without further purification.

MS m/z (ESI): 345.9 [M−1]

Step 3

6-amino-1-(2-fluoro-4-iodophenyl)pyrimidine-2,4(1H,3H)-dione

The crude 2-cyano-N-((2-fluoro-4-iodophenyl)carbamoyl)acetamide 1c (156 g, 430 mmol) was dissolved in 628 mL of water, followed by addition of 2 M sodium hydroxide solution (22.6 mL, 42 mmol). The reaction solution was warmed up to 85° C. and stirred for 1 hour. After cooling down to 0° C., the reaction solution was added dropwise with 2 M hydrochloric acid to adjust the pH to 3, followed by addition of 300 mL of isopropanol, and filtered. The filter cake was washed with water (200 mL×2) and isopropanol (100 mL×3) successively, and dried to obtain the crude title compound 6-amino-1-(2-fluoro-4-iodophenyl)pyrimidine-2,4(1H,3H)-dione 1d (128 g, white solid), which was used directly in the next step without further purification.

MS m/z (ESI): 348.0 [M+1]

Step 4

(E)-N'-(3-(2-fluoro-4-iodophenyl)-2,6-dioxo-1,2,3,6-tetrahydropyrimidin-4-yl)-N,N-dimethylformamidine The crude 6-amino-1-(2-fluoro-4-iodophenyl)pyrimidine-2,4(1H,3H)-dione 1d (128 g, 368.80 mmol) was dissolved in 250 mL of N,N-dimethylformamide, followed by addition of N,N-dimethylformamide dimethyl acetal (124 mL, 935 mmol), and stirred for 4.5 hours. The reaction solution was added with 720 mL of a mixed solution of water and isopropanol (V:V=5:1), stirred for 1 hour, and filtered. The filter cake was washed with water (200 mL×2) and isopropanol (50 mL×2) successively, and dried to obtain the crude title compound (E)-N'-(3-(2-fluoro-4-iodophenyl)-2,6-dioxo-1,2,3,6-tetrahydropyrimidin-4-yl)-N,N-dimethylformamidine 1e (132 g, white solid), which was used directly in the next step without further purification.

MS m/z (ESI): 403.0 [M+1]

Step 5

(E)-N'-(3-(2-fluoro-4-iodophenyl)-1-(4-methoxybenzyl)-2,6-dioxo-1,2,3,6-tetrahydropyrimidin-4-yl)-N,N-dimethylformamidine The crude (E)-N'-(3-(2-fluoro-4-iodophenyl)-2,6-dioxo-1,2,3,6-tetrahydropyrimidin-4-yl)-N,N-dimethylformamidine 1e (20 g, 50 mmol) was dissolved in 150 mL of N,N-dimethylformamide, followed by addition of 1,8-diazabicyclo[5.4.0]undec-7-ene (22.4 mL, 150 mmol) and 4-methoxybenzyl chloride (14.1 mL, 104.30 mmol). The reaction solution was warmed up to 75° C. and stirred for 3 hours. After cooling down to room temperature, the reaction solution was added with 675 mL of a mixed solution of water and isopropanol (V:V=2:1), stirred for 1 hour and filtered. The filter cake was washed with water (200 mL×2) and isopropanol (50 mL×2) successively, and dried to obtain the crude title compound (E)-N'-(3-(2-fluoro-4-iodophenyl)-1-(4-methoxybenzyl)-2,6-dioxo-1,2,3,6-tetrahydropyrimidin-4-yl)-N,N-dimethylformamidine 1f (35 g, white solid), which was used directly in the next step without further purification.

MS m/z (ESI): 523.0 [M+1]

Step 6

1-(2-fluoro-4-iodophenyl)-3-(4-methoxybenzyl)-6-(methylamino)pyrimidine-2,4(1H,3H)-dione Sodium borohydride (3.80 g, 100 mmol) was dissolved in 210 mL of a mixed solution of ethanol and tert-butanol (V:V=1:2), followed by addition of the crude (E)-N'-(3-(2-fluoro-4-iodophenyl)-1-(4-methoxybenzyl)-2,6-dioxo-1,2,3,6-tetrahydropyrimidin-4-yl)-N,N-dimethylformamidine 1f (35 g, 67 mmol). The reaction solution was warmed up to 65° C. and stirred for 1 hour. After cooling down to 0° C., the reaction solution was added with 175 mL of water and 140 mL of 10% citric acid successively, and filtered. The filter cake was washed with water (200 mL×2) and isopropanol (50 mL×2) successively, and dried to obtain the crude title compound 1-(2-fluoro-4-iodophenyl)-3-(4-methoxybenzyl)-6-(methylamino)pyrimidine-2,4(1H,3H)-dione 1g (33 g, white solid), which was used directly in the next step without further purification.

MS m/z (ESI): 482.0 [M+1]

Step 7

1-(2-fluoro-4-iodophenyl)-5-hydroxy-3-(4-methoxybenzyl)-8-methylpyrido[2,3-d]pyrimidine-2,4,7(1H,3H,8H)-trione The crude 1-(2-fluoro-4-iodophenyl)-3-(4-methoxybenzyl)-6-(methylamino)pyrimidine-2,4(1H,3H)-dione 1g (10.80 g, 22.44 mmol) and diethyl malonate (21.20 g, 157.09 mmol) were dissolved in 100 mL of phenyl ether. The reaction solution was warmed up to 230° C. and stirred for 1 hour. After cooling down to room temperature, the reaction solution was concentrated under reduced pressure, and the resulting residue was purified by silica gel column chromatography with elution system B to obtain the title compound 1-(2-fluoro-4-iodophenyl)-5-hydroxy-3-(4-methoxybenzyl)-8-methylpyrido[2,3-d]pyrimidine-2,4,7(1H,3H,8H)-trione 1h (8.97 g, orange solid), yield: 72.9%.

MS m/z (ESI): 550.0 [M+1]

Step 8

1-(2-fluoro-4-iodophenyl)-3-(4-methoxybenzyl)-8-methyl-2,4,7-trioxo-pyrido[2,3-d]pyrimidin-5-yl trifluoromethanesulfonate 1-(2-fluoro-4-iodophenyl)-5-hydroxy-3-(4-methoxybenzyl)-8-methylpyrido[2,3-d]pyrimidine-2,4,7(1H,3H,8H)-trione 1h (8.97 g, 16.33 mmol) was dissolved in 100 mL of dichloromethane, followed by addition of triethylamine (7.00 g, 65.32 mmol). After cooling down to 0° C., the reaction solution was added with trifluoromethanesulfonic anhydride (9.21 g, 32.66 mmol), then warmed up to room temperature and stirred for 3 hours. The reaction solution was concentrated under reduced pressure, and the resulting residue was purified by silica gel column chromatography with elution system B to obtain the title compound 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (4.13 g, yellow solid), yield: 37.1%.

MS m/z (ESI): 682.0 [M+1]

Step 9

5-(6-methylpyridin-3-yloxy)-1-(2-fluoro-4-iodophenyl)-3-(4-methoxybenzyl)-8-methylpyrido[2,3-d]pyrimidine-2,4,7(1H,3H,8H)-trione 6-methyl-3-hydroxy-pyridine (26 mg, 0.24 mmol) was dissolved in 5 mL of tetrahydrofuran, followed by addition of sodium hydride (12 mg, 0.30 mmol). After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), and warmed up to 60° C. and stirred for 1 hour. The reaction solution was concentrated under reduced pressure to obtain the crude title compound 5-(6-methylpyridin-3-yloxy)-1-(2-fluoro-4-iodophenyl)-3-(4-methoxybenzyl)-8-methylpyrido[2,3-d]pyrimidine-2,4,7(1H,3H,8H)-trione 31a (128 mg, pale yellow liquid), which was used directly in the next step without further purification.

MS m/z (ESI): 641.1 [M+1]

Step 10

4-(6-methylpyridin-3-yloxy)-2-(2-fluoro-4-iodophenylamino)-N-(4-methoxybenzyl)-1-methyl-6-oxo-1,6-dihydropyridine-3-carboxamide The crude 5-(6-methylpyridin-3-yloxy)-1-(2-fluoro-4-iodophenyl)-3-(4-methoxybenzyl)-8-methylpyrido[2,3-d]pyrimidine-2,4,7(1H,3H,8H)-trione 1k (128 mg, 0.20 mmol) was dissolved in 6 mL of a mixed solution of tetrahydrofuran and water (V:V=4:1), followed by addition of lithium hydroxide (168 mg, 4 mmol). The reaction solution was warmed up to 40° C. and stirred for 1 hour, followed by addition of 50 mL of ethyl acetate. The organic phase was washed with 1 M sodium hydroxide solution (30 mL×3), dried over anhydrous sodium sulfate, filtered, and the filtrate was concentrated under reduced pressure to obtain the crude title compound 4-(6-methylpyridin-3-yloxy)-2-(2-fluoro-4-iodophenylamino)-N-(4-methoxybenzyl)-1-methyl-6-oxo-1,6-dihydropyridine-3-carboxamide 1l (123 mg, brown oil), which was used directly in the next step without further purification.

MS m/z (ESI): 615.0 [M+1]

Step 11

4-(6-methylpyridin-3-yloxy)-2-(2-fluoro-4-iodophenylamino)-1-methyl-6-oxo-1,6-dihydropyridine-3-carboxamide The crude 4-(6-methylpyridin-3-yloxy)-2-(2-fluoro-4-iodophenylamino)-N-(4-methoxybenzyl)-1-methyl-6-oxo-1,6-dihydropyridine-3-carboxamide 1l (123 mg, 0.20 mmol) was dissolved in 5 mL of anisole, followed by addition of aluminum chloride (133 mg, 1 mmol). The reaction solution was warmed up to 120° C. and stirred for 4 hours, followed by addition of 50 mL of ethyl acetate and 15 mL of water. The organic phase was washed with water (25 mL×3), dried over anhydrous sodium sulfate, and filtered. The filtrate was concentrated under reduced pressure, and the resulting residue was purified by preparative separation method to obtain the title compound 2-(2-fluoro-4-iodophenylamino)-1-methyl-4-(6-methylpyridin-3-yloxy)-6-oxo-1,6-dihydropyridine-3-carboxamide 1 (30 mg, light brown solid), yield: 30.3%.

MS m/z (ESI): 495.0 [M+1]

$^1$H NMR (400 MHz, DMSO-$d_6$): δ 9.78 (s, 1H), 8.38-8.44 (m, 1H), 7.57-7.75 (m, 4H), 7.35-7.49 (m, 2H), 6.65 (t, 1H), 5.09 (s, 1H), 3.15 (s, 3H), 2.51 (s, 3H).

Example 2

Figure 2:
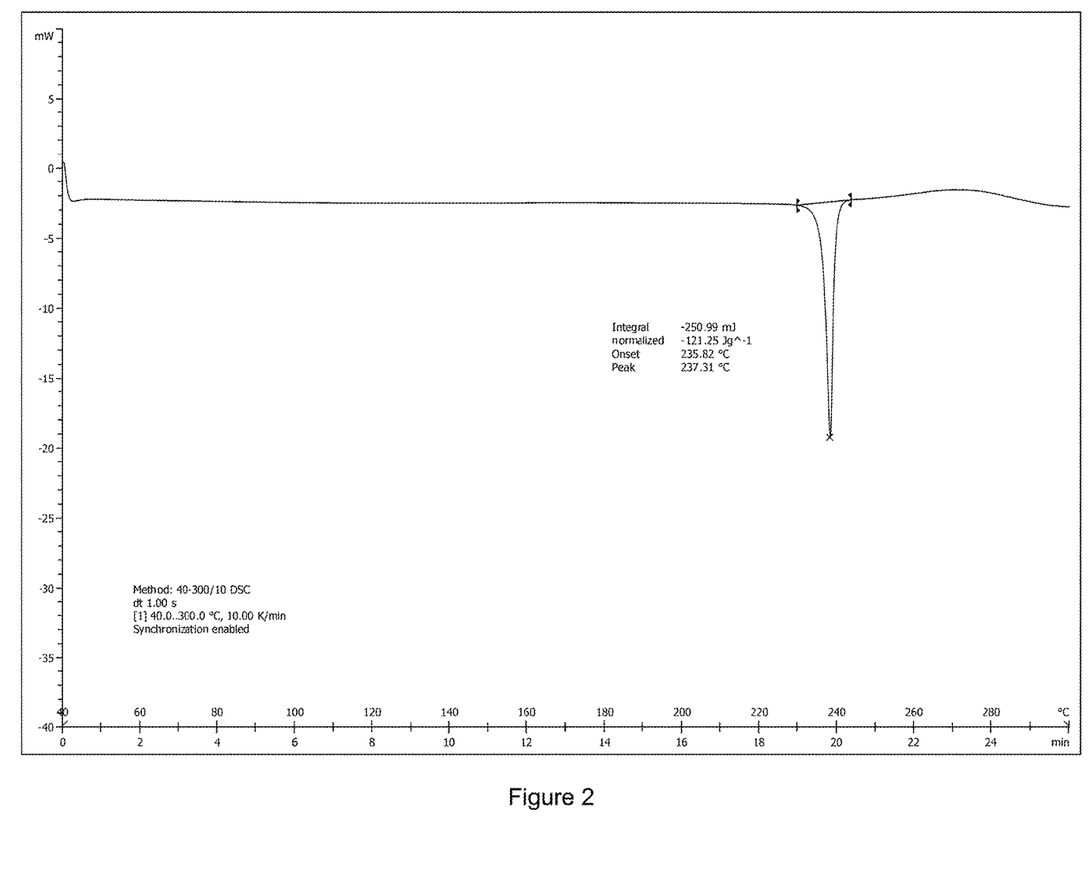
FIG. 2 shows the DSC spectrum of crystal form I of the compound of formula (I).

2-((2-fluoro-4-iodophenyl)amino)-1-methyl-4-((6-methylpyridin-3-yl)oxy)-6-oxo-1,6-dihydropyridine-3-carboxamide (1 g, 2.02 mmol), p-toluenesulfonic acid (0.39 g, 2.27 mmol) and isopropanol (20.41 g) were added to a flask, and refluxed for 2-2.5 h. The heating was stopped, and the reaction mixture was stirred continuously for 12-14 h. The reaction was terminated and filtered, and the filter cake was washed with isopropanol (100 g), and dried at 40-45° C. under reduced pressure for 6-7 hours to obtain a solid (1.10 g) in a yield of 81.6%. The X-ray powder diffraction spectrum of the crystal sample is shown in FIG. 1, in which there are characteristic peaks at about 10.18 (8.68), 11.51 (7.68), 12.34 (7.17), 12.97 (6.82), 13.72 (6.45), 14.83 (5.97), 15.76 (5.62), 17.13 (5.17), 17.59 (5.04), 17.92 (4.95), 18.50 (4.79), 19.72 (4.50), 20.03 (4.43), 20.42 (4.35), 21.04 (4.22), 21.51 (4.13), 21.88 (4.06), 23.15 (3.84), 24.14 (3.68), 24.53 (3.63), 24.77 (3.59), 25.88 (3.44) and 26.37 (3.38). The DSC spectrum is shown in FIG. 2, having a sharp melting endothermic peak at about 237° C. The crystal form was defined as crystal form I.

Example 3

The compound of formula (I) (1.0 g, 1.50 mmol) (prepared according to Example 2) was added to a 50 mL one-necked flask, and dissolved in 28 mL of methanol under heating. The mixture was cooled to room temperature to precipitate a crystal under stirring. The mixture was filtered and dried in a vacuum to obtain a solid (0.30 g, yield: 30.0%). The product was identified as crystal form I after studying and comparing the X-ray diffraction and DSC spectra.

Example 4

The compound of formula (I) (1.0 g, 1.50 mmol) (prepared according to Example 2) was added to a 250 mL one-necked flask, and dissolved in 100 mL of ethanol under heating. The mixture was cooled to room temperature to precipitate a crystal under stirring. The mixture was filtered and dried in a vacuum to obtain a solid (0.40 g, yield: 40.0%). The product was identified as crystal form I after studying and comparing the X-ray diffraction and DSC spectra.

Example 5

The compound of formula (I) (1.0 g, 1.50 mmol) (prepared according to Example 2) was added to a 25 mL one-necked flask, and dissolved in 6 mL of 95% methanol under heating. The mixture was cooled to room temperature to precipitate a crystal under stirring. The mixture was filtered and dried in vacuum to obtain a solid (0.48 g, yield: 48.0%). The product was identified as crystal form I after studying and comparing the X-ray diffraction and DSC spectra.

Example 6

The compound of formula (I) (1.0 g, 1.50 mmol) (prepared according to Example 2) was added to a 50 mL one-necked flask, and dissolved in 24 mL of 95% ethanol under heating. The mixture was cooled to room temperature to precipitate a crystal under stirring. The mixture was filtered and dried in a vacuum to obtain a solid (0.50 g, yield: 50.0%). The product was identified as crystal form I after studying and comparing the X-ray diffraction and DSC spectra.

Example 7

The compound of formula (I) (1.0 g, 1.50 mmol) (prepared according to Example 2) was added to a 50 mL one-necked flask, and dissolved in 18 mL of 90% isopropanol under heating. The mixture was cooled to room temperature to precipitate a crystal under stirring. The mixture was filtered and dried in a vacuum to obtain a solid (0.48 g, yield: 48.0%). The product was identified as crystal form I after studying and comparing the X-ray diffraction and DSC spectra.

Example 8

The compound of formula (I) (1.0 g, 1.50 mmol) (prepared according to Example 2) was added to a 50 mL one-necked flask, and dissolved in 12 mL of 90% acetonitrile under heating. The mixture was cooled to room temperature to precipitate a crystal under stirring. The mixture was filtered and dried in a vacuum to obtain a solid (0.46 g, yield: 46.0%). The product was identified as crystal form I after studying and comparing the X-ray diffraction and DSC spectra.

Example 9

The compound of formula (I) (1.0 g, 1.50 mmol) (prepared according to Example 2) was added to a 50 mL one-necked flask, and dissolved in 28 mL of 95% tetrahydrofuran under heating. The mixture was cooled to room temperature to precipitate a crystal under stirring. The mixture was filtered and dried in a vacuum to obtain a solid (0.70 g, yield: 70.0%). The product was identified as crystal form I after studying and comparing the X-ray diffraction and DSC spectra.

Example 10

The compound of formula (I) (1.0 g, 1.50 mmol) (prepared according to Example 2) was added to a 50 mL one-necked flask, and dissolved in 20 mL of 90% acetone under heating. The mixture was cooled to room temperature to precipitate a crystal under stirring. The mixture was filtered and dried in a vacuum to obtain a solid (0.54 g, yield: 54.0%). The product was identified as crystal form I after studying and comparing the X-ray diffraction and DSC spectra.

Example 11

The compound of formula (I) (1.0 g, 1.50 mmol) (prepared according to Example 2) was added to a 50 mL one-necked flask, followed by addition of 20 mL of 90% acetone. The mixture was heated to reflux until the solution was clear. The solution was cooled to room temperature, and 40 mL of acetone was added during the cooling process to precipitate a crystal under stirring. On the next day, the mixture was filtered and dried to obtain a white solid (710 mg, yield: 71.0%).

Example 12

The product sample of crystal form I prepared in Example 2 was spread flat in the air, to test its stability under conditions of lighting, heating (40° C., 60° C.), and high humidity (RH 75%, RH 90%). Samplings were carried out on Day 5 and Day 10. The purity as detected by HPLC is shown in Table 1.

TABLE 1

Stability of crystal form I of the compound of formula (I)

| Batch number | Time (day) | 4500 Lux | 40° C. | 60° C. | RH75% | RH90% |
|---|---|---|---|---|---|---|
| S011312140508 | 0 | 98.86% | 98.86% | 98.86% | 98.86% | 98.86% |
| | 5 | 99.08% | 98.85% | 98.89% | 98.88% | 98.86% |
| | 10 | 99.17% | 98.88% | 98.88% | 98.88% | 98.88% |

After crystal form I of the compound of formula (I) was spread flat in the air under conditions of lighting, heating, and high humidity, the results of the stability study showed that lighting, high humidity and high temperature do not have much effect on the quality of the product, and demonstrated that the crystal form I has good stability.

Example 13

Crystal form I of the compound of formula (I) prepared according to the method of Example 2 was ground, heated and pressed. The results showed that the crystal form is stable. The detailed experimental data are shown in Table 2 below.

TABLE 2

Special stability study of crystal form I of the compound of formula (I)

| Batch number | Treatment Process | Experimental procedure | Crystal form | DSC peak |
|---|---|---|---|---|
| S011312140508G | Grinding treatment for 10 min | 1 g sample of crystal form I of the compound of formula (I) was ground for 10 min in a mortar under nitrogen atmosphere. | Crystal form I | DSC peak 237.66° C. |
| S011312140508H | Heating treatment for 3 h at 80° C. | 1 g sample of crystal form I of the compound of formula (I) was spread flat and heated at 80° C. for 3 h. | Crystal form I | DSC peak 237.45° C. |
| S011312140508P | Pressing treatment | Sample of crystal form I of the compound of formula (I) was pressed to a slice. | Crystal form I | DSC peak 237.75° C. |

What is claimed is:

1. A crystal form I of 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I), wherein the crystal has a characteristic X-ray powder diffraction spectrum comprising diffraction peaks at diffraction angles (2θ) of about 10.18, 17.13, 17.59, 21.51, and 21.88.

2. A method of preparing the crystal form I of the 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I) according to claim 1 comprising the following steps of:

(a) dissolving p-toluenesulfonic acid and 2-((2-fluoro-4-iodophenyl)amino)-1-methyl-4-((6-methylpyridin-3-yl)oxy)-6-oxo-1,6-dihydropyridine-3-carboxamide, or a crystal form or amorphous form of the 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I) in an organic solvent or a mixed solvent of an organic solvent and water to precipitate a crystal, wherein the organic solvent is selected from the group consisting of alcohols, ketones, nitriles, ethers having 1 to 3 carbon atoms, and mixtures thereof; and (b) filtering the crystal, then washing and drying it.

3. The method according to claim 2, wherein the organic solvent in step (a) is selected from the group consisting of methanol, ethanol, isopropanol, and mixtures thereof; and the mixed solvent of the organic solvent and water is selected from the group consisting of methanol/water, ethanol/water, isopropanol/water, acetonitrile/water, acetone/water and tetrahydrofuran/water.

4. The method of claim 3, wherein the single solvent is isopropanol and the mixed solvent is acetone/water.

5. The crystal form (I) of the 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I) according to claim 1, further comprising diffraction peaks at diffraction angles 2θ of about 11.51, 12.34, 12.97, 13.72, 14.83, 15.76, 17.92, 18.50, 19.72, 20.03, 20.42, 21.04, 23.15, 24.14, 24.53, 24.77, 25.88 and 26.37.

6. The crystal form (I) of the 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I) according to claim 5, wherein the crystal form has the following interplanar spacing (Å) at each of the indicated diffraction angles (2θ):

| 2θ(°) | Interplanar Spacing (Å) |
|---|---|
| 10.18 | 8.68 |
| 11.51 | 7.68 |
| 12.34 | 7.17 |
| 12.97 | 6.82 |
| 13.72 | 6.45 |
| 14.83 | 5.97 |
| 15.76 | 5.62 |
| 17.13 | 5.17 |
| 17.59 | 5.04 |
| 17.92 | 4.95 |
| 18.50 | 4.79 |
| 19.72 | 4.50 |
| 20.03 | 4.43 |
| 20.42 | 4.35 |
| 21.04 | 4.22 |
| 21.51 | 4.13 |
| 21.88 | 4.06 |
| 23.15 | 3.84 |
| 24.14 | 3.68 |
| 24.53 | 3.63 |
| 24.77 | 3.59 |
| 25.88 | 3.44 |
| 26.37 | 3.38. |

7. The crystal form (I) of the 2-((2-fluoro-4-iodophenyl) amino)-1-methyl-4-((6-methylpyridin-3-yl)oxy)-6-oxo-1,6-dihydropyridine-3-carboxamide p-toluenesulfonate of formula (I) according to claim 1, wherein a melting point of the crystal form is about 237° C.

8. The crystal form (I) of the 2-((2-fluoro-4-iodophenyl) amino)-1-methyl-4-((6-methylpyridin-3-yl)oxy)-6-oxo-1,6-dihydropyridine-3-carboxamide p-toluenesulfonate of formula (I) according to claim 1, wherein the crystal form has an X-ray powder diffraction spectrum as shown in FIG. 1.

9. A pharmaceutical composition comprising the crystal form (I) of the 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I) according to claim 1, and a pharmaceutically acceptable carrier.

10. A method of inhibiting MEK kinase in a subject, the method comprising administering to the subject the pharmaceutical composition of claim 9.

11. A method of treating melanoma in a subject in need thereof, the method comprising administering to the subject the pharmaceutical composition of claim 9.

12. A pharmaceutical composition comprising the crystal form (I) of the 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I) according to claim 8, and a pharmaceutically acceptable carrier.

13. A method of inhibiting MEK kinase in a subject, the method comprising administering to the subject the pharmaceutical composition of claim 12.

14. A method of treating melanoma in a subject in need thereof, the method comprising administering to the subject the pharmaceutical composition of claim 12.

15. A method of inhibiting MEK kinase in a subject, the method comprising administering to the subject the crystal form (I) of the 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I) according to claim 1.

16. A method of inhibiting MEK kinase in a subject, the method comprising administering to the subject the crystal form (I) of the 2-((2-fluoro-4-iodophenyl)amino)-1-methyl-4-((6-methylpyridin-3-yl)oxy)-6-oxo-1,6-dihydropyridine-3-carboxamide p-toluenesulfonate of formula (I) according to claim 8.

17. A method of treating melanoma in a subject in need thereof, the method comprising administering to the subject the crystal form (I) of the 2-((2-fluoro-4-iodophenyl) amino)-1-methyl-4-((6-methylpyridin-3-yl)oxy)-6-oxo-1,6-dihydropyridine-3-carboxamide p-toluenesulfonate of formula (I) according to claim 1.

18. A method of treating melanoma in a subject in need thereof, the method comprising administering to the subject the crystal form (I) of the 2-((2-fluoro-4-iodophenyl) amino)-1-methyl-4-((6-methylpyridin-3-yl)oxy)-6-oxo-1,6-dihydropyridine-3-carboxamide p-toluenesulfonate of formula (I) according to claim 8.

* * * * *